United States Patent
Huang

(10) Patent No.: US 9,763,804 B1
(45) Date of Patent: Sep. 19, 2017

(54) BONE FUSION DEVICE

(71) Applicant: OSSAWARE BIOTECH CO., LTD., Changhua County (TW)

(72) Inventor: Max Huang, Changhua County (TW)

(73) Assignee: OSSAWARE BIOTECH CO., LTD., Changhua County (TW)

(*) Notice: Subject to any disclaimer, the term of this patent is extended or adjusted under 35 U.S.C. 154(b) by 0 days.

(21) Appl. No.: 15/067,187

(22) Filed: Mar. 11, 2016

(51) Int. Cl.
*A61F 2/44* (2006.01)

(52) U.S. Cl.
CPC ............ *A61F 2/4455* (2013.01); *A61F 2/442* (2013.01); *A61F 2/447* (2013.01); *A61F 2002/4475* (2013.01); *A61F 2220/0008* (2013.01)

(58) Field of Classification Search
CPC .............................................. A61F 2/44–2/447
See application file for complete search history.

(56) References Cited

U.S. PATENT DOCUMENTS

| | | | | |
|---|---|---|---|---|
| 8,523,946 B1* | 9/2013 | Swann | ............... | A61F 2/447 623/17.11 |
| 2005/0113917 A1* | 5/2005 | Chae | ............... | A61F 2/446 623/17.11 |
| 2014/0039623 A1* | 2/2014 | Iott | ............... | A61F 2/30744 623/17.16 |
| 2014/0288653 A1* | 9/2014 | Chen | ............... | A61F 2/447 623/17.16 |
| 2014/0343678 A1* | 11/2014 | Suddaby | ............... | A61F 2/46 623/17.16 |
| 2015/0012097 A1* | 1/2015 | Ibarra | ............... | A61F 2/447 623/17.15 |

* cited by examiner

*Primary Examiner* — Nicholas Plionis
(74) *Attorney, Agent, or Firm* — Leong C. Lei

(57) ABSTRACT

A bone fusion device includes a main body and a movable frame. The main body has an accommodation hole. A top surface and a bottom surface of the main body are provided with a plurality of first teeth. The movable frame is located in the accommodation hole. The movable frame has a through hole longitudinally penetrating a first surface and a second surface thereof. A first end of the movable frame is fixed to the front end of the main body, and a second end is suspended relative to the rear end of the main body. The first surface and the second surface are provided with a plurality of second teeth. The movable frame is transversely formed with a groove to define an upper portion and a lower portion, enabling the upper portion and the lower portion to be elastically expanded with the first end as a fulcrum.

12 Claims, 11 Drawing Sheets

BONE FUSION DEVICE

BACKGROUND OF THE INVENTION (a) Technical Field of the Invention

The present invention relates to a bone fusion device, and more particularly to a bone fusion device able to generate a micro motion to help bones grow and to provide a stable engagement.

(b) Description of the Prior Art

Normally, a bone fusion surgery is used for solving the degeneration of the spinal bones or facet joints due to agedness or other external causes.

As disclosed in Taiwan Patent application number 104208837 titled "spinal fusion device", 103220076 titled "implantable artificial intervertebral structure", 100119603 titled "spinal implant and device thereof", 101202457 titled "cervical vertebra fusion device", and so on, the teeth on the top and bottom surfaces of a main body provide an acting force for propping two bones (the vertebra or the joints) to a predetermined distance.

Wolff's law states that bone in a healthy person or animal will adapt to the loads under which it is placed. If loading on a particular bone increases, the bone will remodel itself over time to become stronger to resist that sort of loading. The devices of the aforesaid patents only provide a single acting force applied to two bones. When the human body is moved, the retaining effect of the device is not stable. More unfortunately, it is unable to bring obvious bone-conducted stimulation, so the efficiency to grow bones needs to be improved.

Accordingly, the inventor of the present invention has devoted himself based on his many years of practical experiences to solve these problems.

SUMMARY OF THE INVENTION

The primary object of the present invention is to provide a bone fusion device. The bone fusion device comprises a main body and a movable frame. The main body has a front end and an opposing rear end, a top surface and an opposing bottom surface, and an accommodation hole longitudinally penetrating the top surface and the bottom surface. The top surface and the bottom surface are provided with a plurality of first teeth. The first teeth are spaced and disposed between the front end and the rear end. The movable frame is located in the accommodation hole. The movable frame has a first end and an opposing second end at front and rear ends thereof, a first surface and a second surface at upper and lower ends thereof, and a through hole longitudinally penetrating the first surface and the second surface. The first end of the movable frame is fixed to the front end of the main body. The second end is suspended relative to the rear end of the main body. The first surface and the second surface are provided with a plurality of second teeth. The second teeth are spaced and disposed between the first end and the second end. The second end of the movable frame is transversely formed with a groove to define an upper portion and a lower portion. The upper portion and the lower portion can be elastically expanded or retracted with the first end as a fulcrum. When the main body is implanted between two bones, the first teeth provide a first acting force, the second teeth provide a second acting force, and the second acting force is not equal to the first acting force.

Accordingly, the second acting force of the second teeth to act on the two bones and the first acting force of the first teeth to act on the two bones are differential and complementary to strengthen the stability of engagement. The first teeth and the second teeth can slightly stimulate the two bones to expedite fusion of the two bones so as to improve the shortcomings of the prior art.

DETAILED DESCRIPTION OF THE PREFERRED EMBODIMENTS

Figure 1:
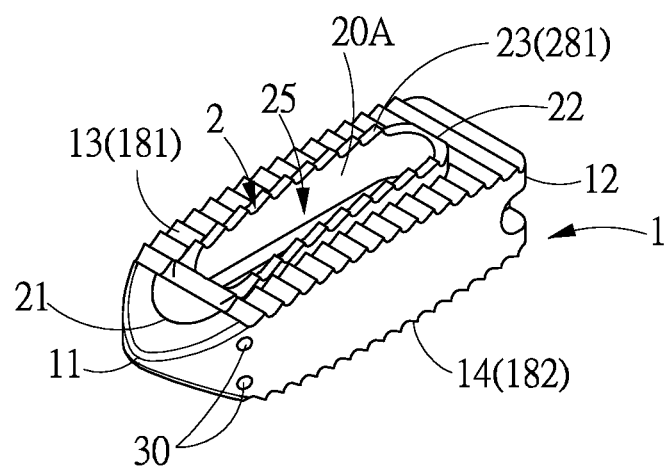
FIG. 1 is a perspective view of the present invention.
Figure 2:
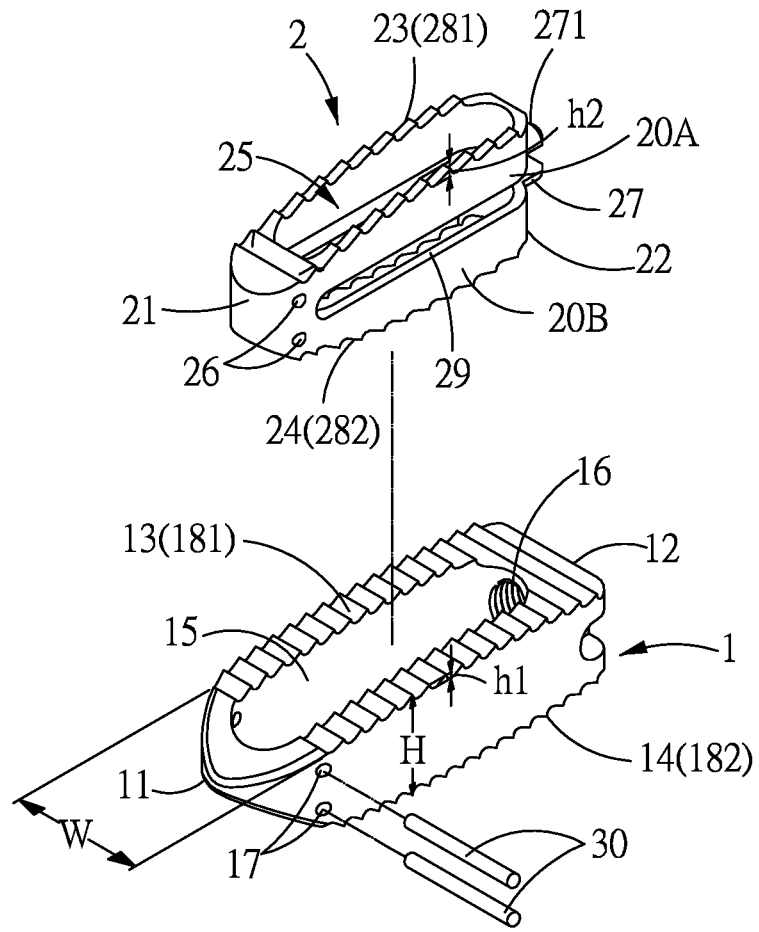
FIG. 2 is an exploded view of the present invention.
Figure 3:
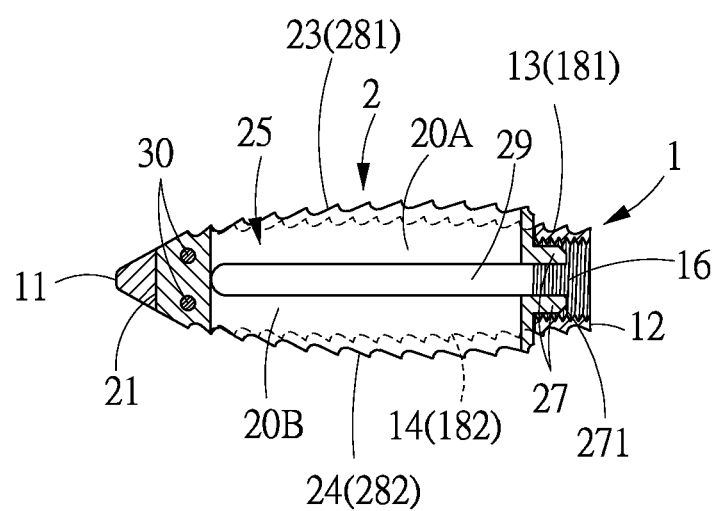
FIG. 3 is a sectional view of the present invention.
Figure 4:
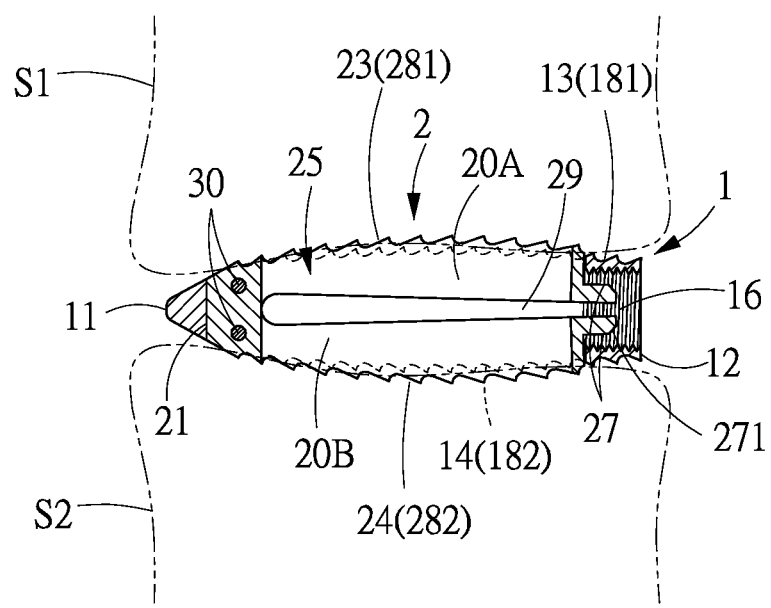
FIG. 4 is a schematic view of the present invention implanted between two bones.
Figure 5:
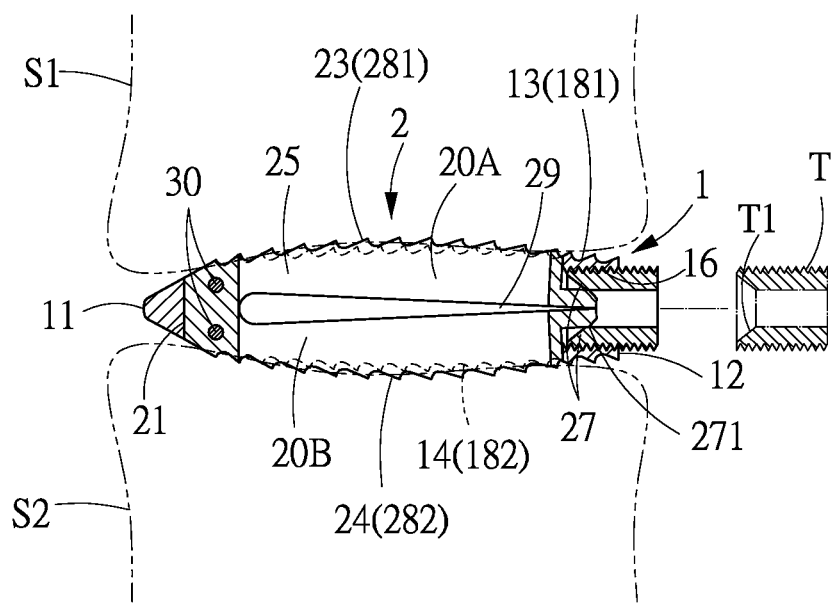
FIG. 5 is a schematic view of a first embodiment of the present invention implanted between two bones.
Figure 6:
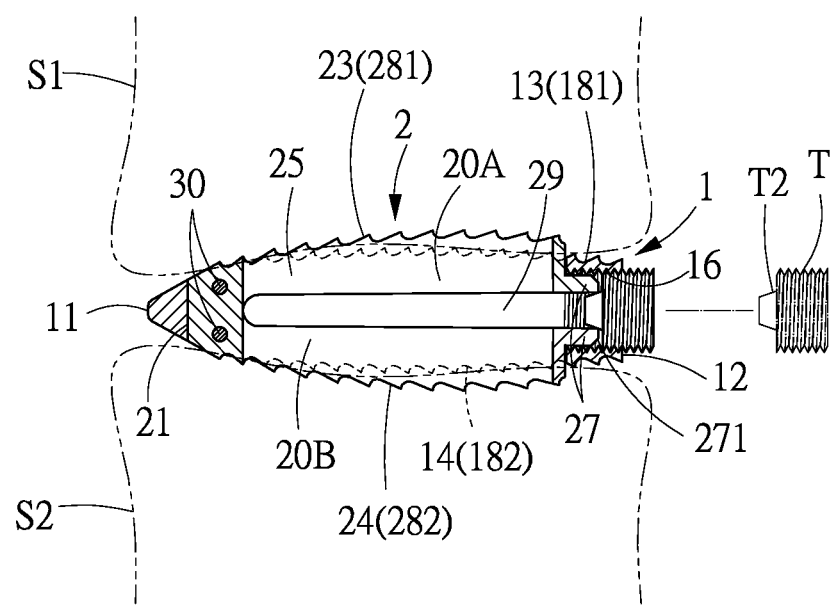
FIG. 6 is a schematic view of a second embodiment of the present invention implanted between two bones.

Embodiments of the present invention will now be described, by way of example only, with reference to the accompanying drawings.

As shown in FIG. 1 through FIG. 4, the present invention comprises a main body 1 and a movable frame 2.

The main body 1 has a front end 11 and an opposing rear end 12. The man body 1 further has a raised curved top surface 13 and a raised curved bottom surface 14. The curvatures of the top surface 13 and the bottom surface 14 are close to the curvatures of two adjacent bones S1, S2 (referring to the spines or joints). A height defined by the top surface 13 and the bottom surface 14 is gradually reduced toward the front end 11 and a width defined by left and right sides of the main body 1 is gradually reduced toward the front end 11, enabling the front end 11 to be easily implanted between the two bones S1, S2. The main body 1 further has an accommodation hole 15 which longitudinally penetrates the top surface 13 and the bottom surface 14 and has a closed side wall. The rear end 12 of the main body 1 is transversely formed with a mounting hole 16 in communication with the accommodation hole 15. The mounting hole 16 has inner threads for screwed engagement of a tool member T. The main body 1 is formed with two first holes 17 which are disposed close to the front end 11 and penetrates the left and right sides of the main body 1. The first holes 17 are in communication with the accommodation hole 15. The top surface 13 and the bottom surface 14 have a plurality of first teeth 181, 182 which are evenly disposed between the front end 11 and the rear end 12. The first teeth 181, 182 are arranged at an equal interval between the front end 11 and the rear end 12. The first teeth 181, 182 are in the form of ratchets and have a tooth height h1 which is gradually reduced toward the front end 11, such that the first teeth 181, 182 cooperate with the front end 11 of the main body 1 to be implanted between the two bones S1, S2 in a one-way manner, providing a first acting force to be implanted between the two bones S1, S2.

The movable frame 2 is inserted into the accommodation hole 15, and has a first end 21 and an opposing second end 22 at front and rear ends thereof. Upper and lower ends of the movable frame 2 have raised curved first and second surfaces 23, 24. The curvatures of the first and second surface 23, 24 are close to the curvatures of the two adjacent bones S1, S2. The movable frame 2 further has a through hole 25 which longitudinally penetrates the first and second surfaces 23, 24 and has a closed side wall. The first end 21 of the movable frame 2 corresponds to the front end 11 of the main body 1, and the second end 22 is suspended relative to the rear end 12 of the main body 1. The first end 21 is formed with second holes 26 corresponding to the first holes 17 for insertion of coupling members 30. The first end 21 is fixed to the front end 11 of the main body 1. The second end 22 is provided with a push post 27 which concentrically extends into the mounting hole 16. An outer wall of the push post 27 has a push surface 271. The first surface 23 and the second surface 24 have a plurality of second teeth 281, 282 which are evenly disposed between the first end 21 and the second end 22. The second teeth 281, 282 are arranged at an equal interval between the first end 21 and the second end 22. The second teeth 281, 282 are in the form of ratchets and have a tooth height h2 which is gradually reduced toward the first end 21. The second teeth 281, 282 and first teeth 181, 182 are disposed in a staggered arrangement, such that the first teeth 181, 182 and the second teeth 281, 282 cooperate with the front end 11 of the main body 1 to be implanted between the two bones S1, S2 in a one-way manner. The movable frame 2 is transversely cut in half from an outer end of the push post 27 to form a groove 29 which doesn't penetrate through the first end 21 of the movable frame 2, such that the movable frame 2 is symmetrically formed with an upper portion 20A and a lower portion 20B. The upper portion 20A and the lower portion 20B can be elastically expanded with the first end 21 as the fulcrum, enabling the second teeth 281, 282 of the first surface 23 and the second surface 24 to provide a second acting force to the two bones S1, S2. The second acting force is not equal to the first acting force to generate a differential complementation, which reinforces the engagement of the main body 1 and the movable frame 2 when the human body is moved. What is important is that the first teeth 181, 182 or the second teeth 281, 282 can slightly friction and stimulate the two bones S1, S2 (bone-conducted stimulation) to expedite fusion of the two bones S1, S2.

Referring to FIG. 1 through FIG. 5, before the present invention is implanted between the two bones S1, S2, the tool member T having a conical hole T1 is screwed to the mounting hole 16. The conical hole T1 of the tool member T is screwedly moved to act on the push surface 271 of the push post 27 for the push post 27 to link the upper portion 20A and the lower portion 20B of the movable frame 2 to retract toward the groove 29, such that the second teeth 281, 282 can be implanted between the two bones S1, S2 smoothly. After implantation, the tool member T is taken out to release the outward expanding elasticity of the second teeth 281, 282.

Referring to FIG. 1, FIG. 2, FIG. 3, FIG. 4, FIG. 6, the second teeth 281, 282 of the movable frame 2 of the present invention is kept within the accommodation hole 15, not extending out of the first teeth 181, 182 for the present invention to be implanted between the two bones S1, S2 as the aforesaid patents. The tool member T having a conical post T2 is screwed to the mounting hole 16. The conical post T2 of the tool member T is screwedly inserted into the groove 29 of the push post 27, enabling the conical post T2 to control the degree of the outward extension of the upper portion 20A and the lower portion 20B of the movable frame 2 and apply a second acting force to the two bones S1, S2. The first acting force and the second acting force are controlled to be differential so as to differentially stimulate the growth of the two bones S1, S2.

Figure 7:
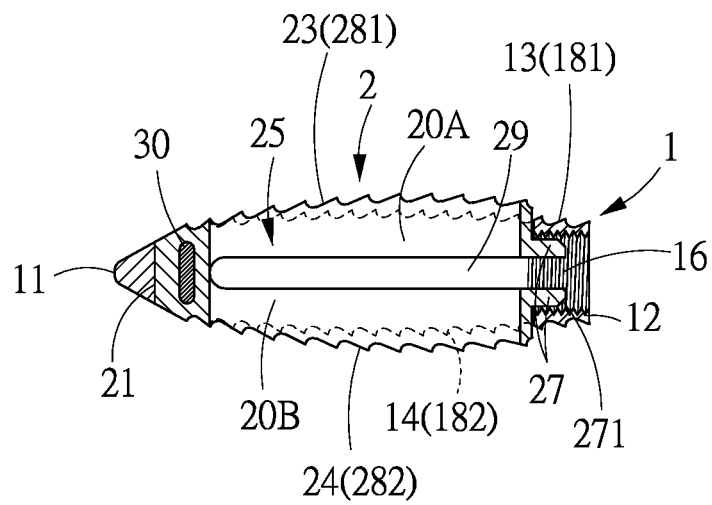
FIG. 7 is a schematic view of a first embodiment of the movable frame fixed to the main body of the present invention.
Figure 8:
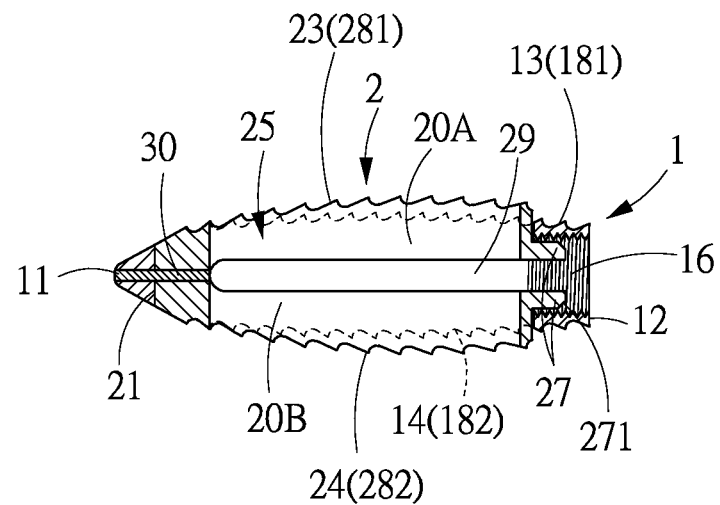
FIG. 8 is a schematic view of a second embodiment of the movable frame fixed to the main body of the present invention.
Figure 9:
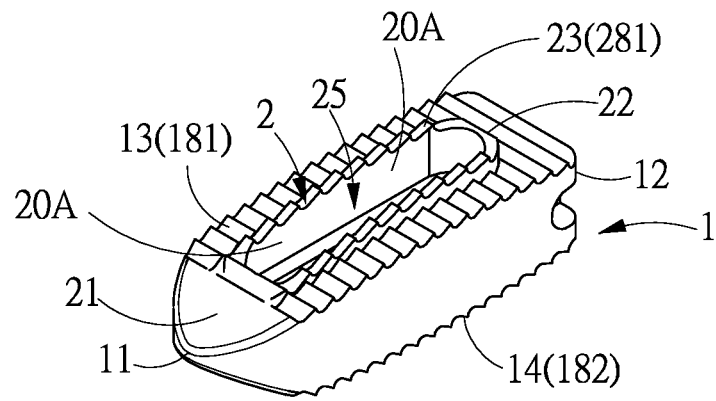
FIG. 9 and FIG. 10 are schematic views of a third embodiment of the movable frame fixed to the main body of the present invention.
Figure 10:
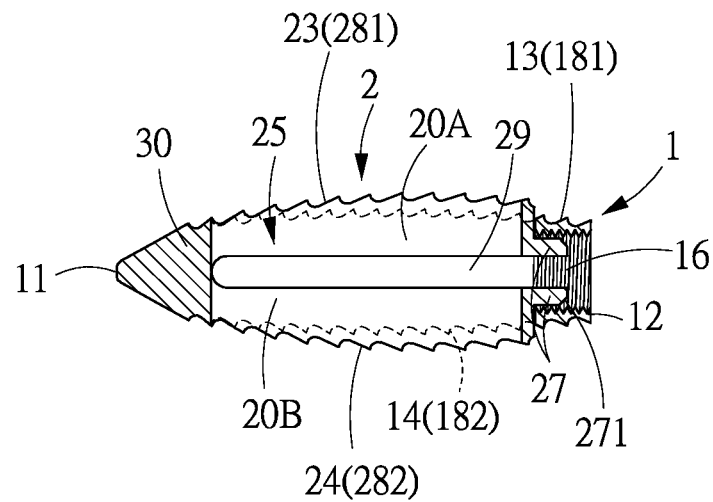

As shown in FIG. 1 and FIG. 7, the shape and the number of the first holes 17, the second holes 26, and the coupling members 30 can be changed. As shown in FIG. 8, the direction of the first holes 17, the second holes 26, and the coupling members 30 are also changed. Specifically, the first end 21 of the movable frame 2 can be fixedly connected to the accommodation hole 15 relative to the position of the front end 11 of the main body 1. This belongs to the present invention. Furthermore, as shown in FIG. 9 and FIG. 10, the movable frame 2 can be integrally formed in the accommodation hole 15 of the main body 1 if the manufacturing technique and the cost are allowed.

Figure 11:
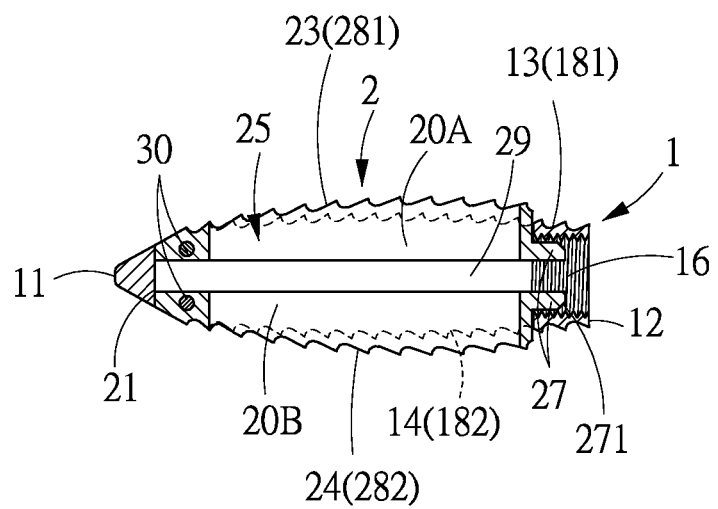
FIG. 11 is a schematic view of a fourth embodiment of the movable frame fixed to the main body of the present invention.

Referring to FIG. 11, the upper portion 20A and the lower portion 20B of the movable frame 2 are separately mounted in the accommodation hole 15 through different coupling members 30, so that the groove 29 is configured to separate the upper portion 20A and the lower portion 20B of the movable frame 2. This also belongs to the present invention.

Figure 12:
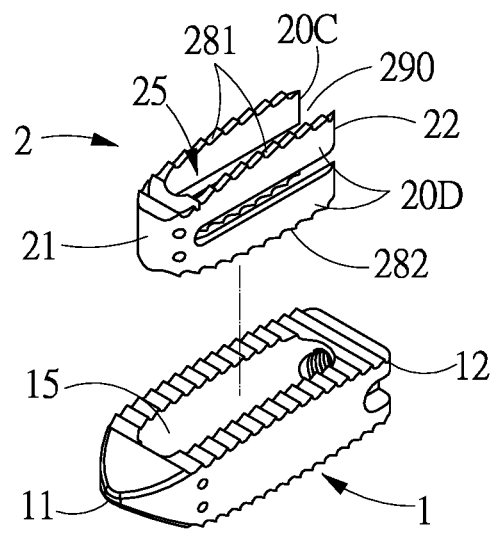
FIG. 12 is a schematic view of another embodiment of the movable frame of the present invention.
Figure 13:
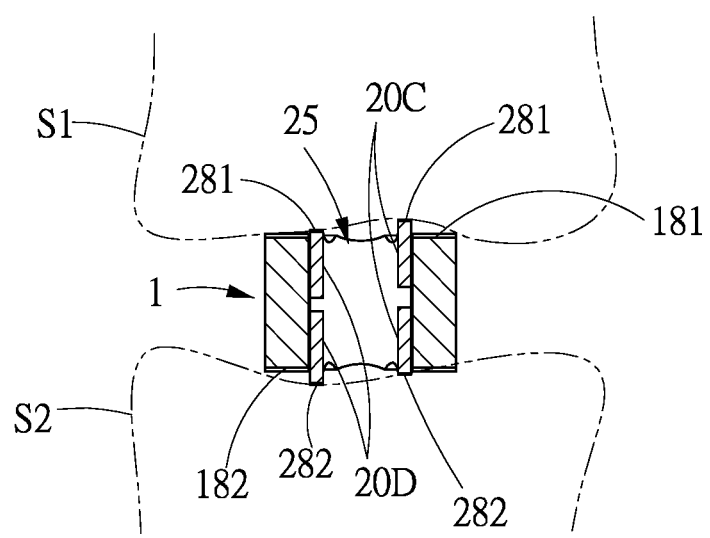
FIG. 13 is a schematic view of the main body and the movable frame implanted between two bones of FIG. 12.
Figure 14:
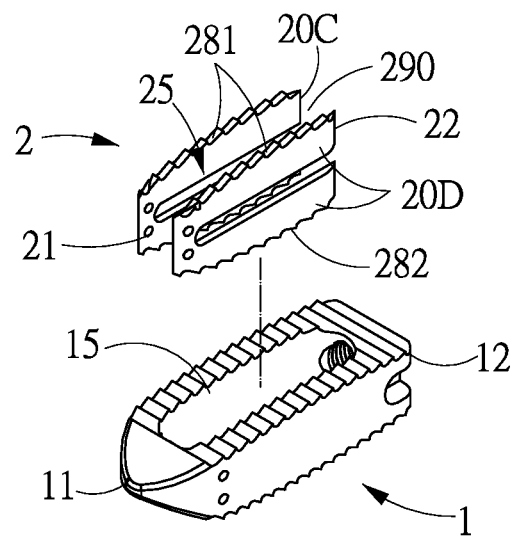
FIG. 14 is a schematic view of a further embodiment of the movable frame of the present invention.
Figure 15:
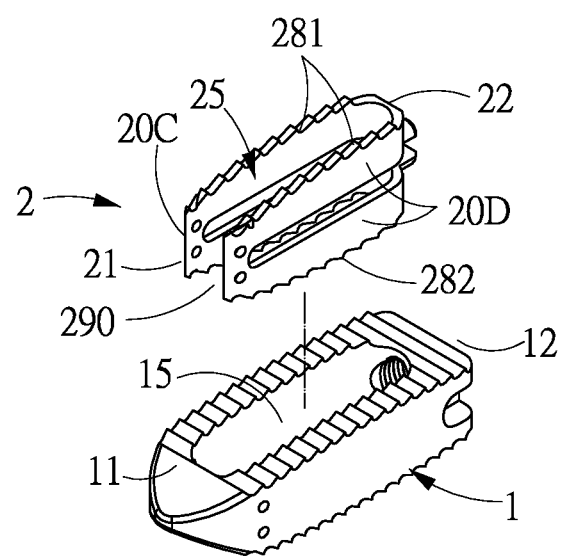
FIG. 15 is a yet schematic view of a further yet embodiment of the movable frame of the present invention.

As shown in FIG. 12, the movable frame 2 is located in the accommodation hole 15. The first end 21 is fixedly connected to the front end 11 of the main body 1, and the second end 22 is suspended relative to the rear end 12 of the main body 1. The movable frame 2 is vertically longitudinally cut in half to form an opening 290 which penetrates the second end 22 but doesn't penetrate the first end 21. The opening 290 is in communication with the through hole 25. The movable frame 2 is symmetrically formed with a left portion 20C and a right portion 20D. The second teeth 281, 282 of the left portion 20C and the right portion 20D can be expanded upward or downward with the first end 21 as the fulcrum. As shown in FIG. 13, when the present invention is implanted between the two bones S1, S2, the second teeth 281, 282 of the left portion C and the second teeth 281, 282 of the right portion D form a differential motion corresponding to the different gaps formed by the two bones S1, S2. When the human body is moved, the second teeth 281, 282 can slightly friction and stimulate the two bones S1, S2 (bone-conducted stimulation) to expedite fusion of the two bones S1, S2. In addition, as shown in FIG. 14, the opening 290 vertically longitudinally penetrates the first end 21 and the second end 22. The left portion 20C and the right portion 20D are separately fixed to the front end 11 of the main body 1. This embodiment enhances the differential motion effect of the second teeth 281, 282 of the left portion 20C and the right portion 20D. As shown in FIG. 15, the movable frame 2 is vertically longitudinally cut in half to form an opening 290 which penetrates the first end 21 but doesn't penetrate the second end 22. The opening 290 is in communication with the through hole 25. The movable frame 2 is symmetrically formed with a left portion 20C and a right portion 20D. This embodiment can slow down the differential motion effect of the second teeth 281, 282 of the left portion 20C and the right portion 20D of FIG. 13. The embodiment of FIG. 15 is equivalent to that of FIG. 1.

Furthermore, the main body 1 and the movable frame 2 can adopt a metallic or high-polymer material. The metallic material is selected from one of titanium, tantalum, cobalt, stainless steel, liquid metal, and nickel. The high-polymer material is selected from one of PEEK, PEKK, PU, PE, carbon fiber, PVC, PC, and PP.

To sum up, the whole arrangement of the present invention is novel. The second acting force of the second teeth to act on the two bones and the first acting force of the first teeth to act on the two bones are differential and complementary to strengthen the stability of engagement. The present invention can slightly stimulate the two bones to expedite fusion of the two bones.

Although particular embodiments of the present invention have been described in detail for purposes of illustration, various modifications and enhancements may be made without departing from the spirit and scope of the present invention. Accordingly, the present invention is not to be limited except as by the appended claims.

I claim:

1. A bone fusion device, comprising:
   a main body, the main body having a front end and an opposing rear end, a top surface and an opposing bottom surface, and an accommodation hole longitudinally penetrating the top surface and the bottom surface; the top surface and the bottom surface being provided with a plurality of first teeth, the first teeth being spaced and disposed between the front end and the rear end; and
   a movable frame located in the accommodation hole, the movable frame having a first end and an opposing second end at front and rear ends thereof, a first surface and a second surface at upper and lower ends thereof, and a through hole longitudinally penetrating the first surface and the second surface; the first end of the movable frame being fixed to the front end of the main body, the second end being suspended relative to the rear end of the main body, the first surface and the second surface being provided with a plurality of second teeth, the second teeth being spaced and disposed between the first end and the second end; the second end of the movable frame being transversely formed with a groove to define an upper portion and a lower portion for the upper portion and the lower portion to be elastically expanded or retracted with the first end as a fulcrum, wherein when the main body is implanted between two bones, the first teeth provide a first acting force, the second teeth provide a second acting force, and the second acting force is not equal to the first acting force;
   wherein the rear end of the main body is transversely formed with a mounting hole in communication with the accommodation hole, the mounting hole has inner threads for screwed engagement of a tool member; the second end of the movable frame is provided with a push post which concentrically extends into a front edge of the mounting hole, and the groove horizontally penetrates the push post in half; an outer wall of the push post has a push surface, the tool member has a conical hole corresponding to the push surface, the conical hole of the tool member is screwedly moved to act on the push surface of the push post for the push post to link the upper portion and the lower portion of the movable frame to retract toward the groove, such that the second teeth can be implanted between the two bones, and the tool member is taken out to release outward expanding elasticity of the second teeth after implantation.

2. The bone fusion device as claimed in claim 1, wherein the movable frame is vertically longitudinally cut in half to form an opening penetrating the second end, the opening is in communication with the through hole, enabling the movable frame to form a left portion and a right portion, and the second teeth of the left portion and the right portion can be elastically expanded with the first end as the fulcrum.

3. The bone fusion device as claimed in claim 2, wherein the movable frame is vertically longitudinally cut in half to form an opening penetrating the first end, and the opening is in communication with the through hole, enabling the movable frame to form a left portion and a right portion.

4. The bone fusion device as claimed in claim 2, wherein the front end of the main body is formed with a first hole, the first hole is in communication with the accommodation hole, and the first end of the movable frame is formed with a second hole corresponding to the first hole for insertion of a coupling member, such that the first end of the movable frame is fixed to the front end of the main body.

5. The bone fusion device as claimed in claim 2, wherein the first end of the movable frame is integrally formed with the front end of the main body.

6. The bone fusion device as claimed in claim 2, wherein the groove is arranged half from the second end of the movable frame toward the first end and selectively penetrates or doesn't penetrate the first end of the movable frame.

7. The bone fusion device as claimed in claim 2, wherein the top surface and the bottom face of the main body are raised and curved, the top surface and the bottom surface have curvatures close to the curvatures of the two bones, a height defined by the top surface and the bottom surface is gradually reduced toward the front end, a width defined by left and right sides of the main body is gradually reduced toward the front end, the first surface and the second surface of the movable frame are raised and curved, the first surface and the second surface have curvatures close to the curvatures of the two bones, the first teeth and the second teeth are in the form of ratchets and have a tooth height which is gradually reduced toward the first end of the main body, such that the first teeth and the second teeth cooperate with the front end of the main body to be implanted between the two bones in a one-way manner.

8. The bone fusion device as claimed in claim 1, wherein the movable frame is vertically longitudinally cut in half to form an opening penetrating the first end, and the opening is in communication with the through hole, enabling the movable frame to form a left portion and a right portion.

9. The bone fusion device as claimed in claim 1, wherein the front end of the main body is formed with a first hole, the first hole is in communication with the accommodation hole, and the first end of the movable frame is formed with a second hole corresponding to the first hole for insertion of a coupling member, such that the first end of the movable frame is fixed to the front end of the main body.

10. The bone fusion device as claimed in claim 1, wherein the first end of the movable frame is integrally formed with the front end of the main body.

11. The bone fusion device as claimed in claim 1, wherein the groove is arranged half from the second end of the movable frame toward the first end and selectively penetrates or doesn't penetrate the first end of the movable frame.

12. The bone fusion device as claimed in claim 1, wherein the top surface and the bottom face of the main body are raised and curved, the top surface and the bottom surface have curvatures close to the curvatures of the two bones, a height defined by the top surface and the bottom surface is gradually reduced toward the front end, a width defined by left and right sides of the main body is gradually reduced toward the front end, the first surface and the second surface of the movable frame are raised and curved, the first surface and the second surface have curvatures close to the curvatures of the two bones, the first teeth and the second teeth are in the form of ratchets and have a tooth height which is gradually reduced toward the first end of the main body, such that the first teeth and the second teeth cooperate with the front end of the main body to be implanted between the two bones in a one-way manner.

* * * * *